United States Patent [19]

Hascoet et al.

[11] Patent Number: 5,509,929
[45] Date of Patent: Apr. 23, 1996

[54] URETHRAL PROBE AND APPARATUS FOR THE THERAPEUTIC TREATMENT OF THE PROSTATE BY THERMOTHERAPY

[75] Inventors: Gérard Hascoet, Paris; François Lacoste, Lyons; Muriel Cathaud, Venissieux; Marian Devonec, Miribel; Paul Perrin, Lyons, all of France

[73] Assignee: Technomed Medical Systems, Vaulx-en-Velin, France

[21] Appl. No.: 957,400

[22] Filed: Oct. 6, 1992

Related U.S. Application Data

[63] Continuation-in-part of Ser. No. 667,847, Mar. 12, 1991, Pat. No. 5,234,004, which is a continuation-in-part of Ser. No. 438,741, Nov. 17, 1989, abandoned.

[30] Foreign Application Priority Data

| Nov. 21, 1988 | [FR] | France | 88 15126 |
| Mar. 12, 1990 | [JP] | Japan | 90 03121 |
| Jul. 6, 1992 | [JP] | Japan | 92 08319 |

[51] Int. Cl.⁶ .................................................. A61N 5/02
[52] U.S. Cl. .................. 607/101; 607/102; 607/105; 607/113; 607/156; 128/736
[58] Field of Search .................... 607/101, 102, 607/105, 113, 116, 154, 156; 128/736

[56] References Cited

U.S. PATENT DOCUMENTS

| 3,154,077 | 10/1964 | Cannon | 128/325 |
| 4,204,549 | 5/1980 | Paglione | 128/784 |
| 4,311,154 | 1/1982 | Sterzer et al. | |
| 4,612,940 | 9/1986 | Kasevich et al. | 128/804 |
| 4,662,383 | 5/1987 | Sogawa et al. | 128/784 |
| 4,676,258 | 6/1987 | Inokuchi et al. | 128/804 |
| 4,700,716 | 10/1987 | Kasevich et al. | 128/804 |
| 4,813,429 | 3/1989 | Eshel et al. | 128/736 |
| 4,823,812 | 4/1989 | Eshel et al. | 128/804 |
| 4,967,765 | 11/1990 | Turner et al. | |
| 5,007,437 | 4/1991 | Sterzer | 128/786 |
| 5,220,927 | 6/1993 | Astrahan et al. | 128/736 X |

FOREIGN PATENT DOCUMENTS

| 105677 | 4/1984 | European Pat. Off. . |
| 0105677 | 4/1984 | European Pat. Off. . |
| 0139607 | 5/1985 | European Pat. Off. . |
| 248758 | 12/1987 | European Pat. Off. . |
| 370890 | 5/1990 | European Pat. Off. . |
| 2639238 | 2/1991 | France . |
| 2207387 | 8/1973 | Germany . |
| 2407559 | 4/1981 | Germany . |
| 3525702 | 1/1987 | Germany . |
| 3534124 | 2/1987 | Germany . |
| 3534124A1 | 4/1987 | Germany . |
| 6233906 | 2/1982 | Japan . |
| 6251633 | 2/1982 | Japan . |
| 63-109152 | 7/1988 | Japan . |
| 8103616 | 12/1981 | WIPO . |
| 8902292 | 3/1989 | WIPO . |
| 8905609 | 6/1989 | WIPO . |
| 07622 | 5/1992 | WIPO . |

OTHER PUBLICATIONS

Pschyrembel Klinisches Wörterbuch, Walter de Gruyter, Berlin, New York, 1986, S. 1368.
Extract from Traité d'Anatomie Humaine, 9th Ed., vol. 5, pp. 246–249 (1949), together with an English translation.
Microwave Applicator for Transurethral Hyperthermia of (List continued on next page.)

*Primary Examiner*—Lee S. Cohen
*Attorney, Agent, or Firm*—Cohen, Pontani, Lieberman & Pavane

[57] ABSTRACT

A urethral probe having a front part and a rear part, and a microwave antenna connected to an external device for generating microwaves. The microwave antenna has its primary active heating part arranged in the urethral probe to be directed onto the prostatic tissues located at least at the level of the bladder neck in the working position.

The urethral probe constitutes an essential element of a device for the therapeutic treatment of tissues by thermotherapy, more particularly tissues of the bladder neck of the bladder of a human being.

35 Claims, 4 Drawing Sheets

OTHER PUBLICATIONS

Benign Prostatic Hyperplasia, Astrahan et al., Int. J. Hyperthermia, 1989, vol. 5, No. 2,283–296.

Temperaturfeldberechnungen zur Hypertermiebehandlung: Forschungsproject No. 01VF020–AK/NT/MT298, Dorner System GmbH, Friedrichshafen, 1982, pp. 25–30.

Endotract Antenna For Application of Hyperthermia to Malignant Lesions, K. Sugimachi et al, Gann, 74, 1983, pp. 622–624.

Radiofrequency–Induced Hyperthermia in the Prostate, J. Scheblicht et al., Journal of Microwave Power, vol. 17(3), 1982, pp. 208–209.

RF Wave Heating by Trial Applicator for Gynecology, Toshimi Hasegawa et al., Proc. 3rd Annual Meeting of the Japanese Society of Hyperthermic Oncology, Nov. 13–15, 1986, Osaka, Japan.

Microwave–Induced Hyperthermia in Cancer Treatment: Apparatus and Preliminary Results, J. Mendecki et al., Int. J. Radiation Oncology, vol. 4, 1978, pp. 1095–1103.

Local Hyperthermia of the Prostate Gland for the Treatment of Benign Prostatic Hyperthrophy and Urinal Retention, A Preliminary Report, A. Lindner et al., British Journal of Urology (1987), 60, pp. 567–571.

Disease of Prostate Treated by Local Microwave Hyperthermia, C. Sevadio et al., Urology, Aug. 1987, vol. XXX, No. 2, pp. 97–99.

Interstitial and Intracavitary Microwave Hyperthermia, B. Stuart Trembly, Hyperthermic Oncology 1988, vol. 2, Proceedings of the 5th International Symposium on Hyperthermic Oncology, Kyoto, Japan, 29th Aug.–3rd Sep. 1988.

Histopathological Observations in the Canine Prostate Treated by Local Microwave Hyperthermia, Z. Lieb et al., The Prostate 8:93–102 (1986).

Hyperthermiochemoradiotherapy and Esophageal Carcinoma, K. Sugimachi et al., Seminars in Surgical Oncology 2:38–44 (1986).

Design and Thermometry of an Intracavitary Microwave Applicator Suitable for Treatment of Some Vaginal and Rectal Cancers, Ding–Jiu Li et al., Int. J. Radiation Oncology Biol. Phys., vol. 10, pp. 2155–2162 (1984).

Microwave Applicators For Localized Hyperthermia Treatment of Cancer of the Prostate, Mendecki et al., Journal of Radiation Oncology, vol. 6, No. 11, pp. 1583–1588, Nov., 1980.

Grand Larousse Universal, p. 8518 (1991), provided with translation.

Anatomie des Menshen, Schiebler et al. (1983).

Proceedings of the IEEE, vol. 72, No. 2, Feb. 1984, New York, pp. 224–225.

Proceedings of the 13th Northeast Bioengineering Conference, Mar. 12–13, 1987, vol. 2, *Sar Evaluation, Etc.*, pp. 390–393.

Harada et al., *Microwave Surgical Treatment of Diseases of Prostate,* Urology, Dec. 1985, vol. XXVI, No. 6, pp. 572–576.

*Transurethral Hyperthermia for BPH: Trial's Goal is to Top 80*
Success, Medical Tribune, Mar. 31, 1988, vol. 19, No. 9.

Carter, S.St.C, F.R.C.S., *Single–Session Transurethral Microwave Thermotherapy for the Treatment of Benign Prostatic Obstruction,* Journal of Endourology, vol. 5, No. 2, 1991.

Devonec, Marian, M.D., *Transurethral Microwave Heating of the Prostate–Or from Hyperthermia to Thermotherapy,* Journal of Endourology, vol. 5, No. 2, 1991.

Blute, Michael L., M.D., *Transurethral Microwave Thermotherapy for Benign Prostatic Hypertrophy,* Mediguide® to Urology, vol. 4, Issue 6.

Carter, S. et al., Prostatron Clinical Program, *Objective Clinical Results of Transurethral Microwave Thermotherapy for Benign Prostatic Obstruction,* 8th World Congress on Endourology and ESWL, Washington, D.C., Aug. 31–Sep. 2, 1990–Nov. 1990.

8th European Microwave Conference, *Multimode Square Waveguide, Etc.,* Stuchly and Stuchly, Sep. 1978, pp. 553–557.

Strohmaier, W. L., *Local Microwave Hyperthermia of Benign Prostatic Hyperplasha,* The Journal of Urology, Oct. 1990, vol. 144.

Devonec, Marian M.D., *Transurethral Microwave Thermotherapy (TUMT) in Patents with Benign Prostatic Hypertrophy,* American Urological Association—May 1990 New Orleans, Louisiana, Oct. 1990.

Carter, S. et al., Prostatron Clinical Program, *The Physics of Transuretral Microwave Thermotherapy (TUMT),* 8th World Congress on Endourology and ESWL, Washington, D.C., Aug. 31–Sep. 2, 1990, Nov. 1990.

MICROWAVE GENERATOR

URETHRAL PROBE AND APPARATUS FOR THE THERAPEUTIC TREATMENT OF THE PROSTATE BY THERMOTHERAPY

This application is a Continuation-in-Part of pending U.S. patent application Ser. No. 07/667,847 of Mar. 12, 1991, now U.S. Pat. No. 5,234,004, the content of which is incorporated herein by reference in its entirety, which is a continuation-in-part of Ser. No. 07/438,741, filed Nov. 12, 1989, now abandoned.

FIELD OF THE INVENTION

In particular, the present invention relates primarily to an urethral probe means and apparatus for the therapeutic treatment of tissues by thermotherapy, and more particularly the tissues located in the periurethral region of the prostate and neck of the bladder, for treating Benign Prostatic Hypertrophy, abbreviated to BPH.

BACKGROUND OF THE INVENTION

It has been known for some time that Benign Prostatic Hypertrophy, abbreviated to BPH, which is the result of natural enlargement of the periurethral glands of the prostate more or less inevitably leads to compression of the urethral canal preventing the patient from urinating normally. To remedy this problem, resection, more particularly periurethrally, using a resecting device, is the safest and most reliable method recognised worldwide as being the standard treatment of BPH.

More recently it was proposed by HARADA et al., in Urology, in December 1985, volume XXVI, no. 6, pages 572 to 576, to perform transurethral thermal resection of the obstructive BPH tissues by inserting a transurethral probe means comprising an antenna emitting microwaves at a frequency of 2450 MHz. Said thermal treatment succeeds in coagulating the prostate tissues starting with the urethral canal, the maximum temperature attained can reach almost 1000° C. This procedure used to require a general anaesthetic on account of the impossibility for the patient to bear the pain caused by the thermal treatment and also the permanent fitting of an urethral catheter for several weeks whilst waiting for the open periurethral wound to heal. It is indicated that diuresis persisted for beween 30 and 60 days in the majority of cases. This method enables full devascularization of the prostatic tissues to be performed and is considered to be of interest in the initial phase before proceeding with prostate resection which is usually a delicate operation on account of profuse bleeding. This method has never found practical application.

The document Medical Tribune of Mar. 31 1988, volume XXIX, no. 9, pages 1, 4, 11, 13 and 14, likewise describes a transurethral probe comprising several microwave-emitting antennas made fast externally with a Foley catheter for treatment of BPH by hyperthermia at a temperature not exceeding 45° C. so as to heat the central part of the prostate therefore necessarily involving the wall of the urethra. Moderate heating to a hyperthermia temperature is recommended according to a treatment procedure of between 5 and 10 one-hour sessions, once or twice a week, which is extremely traumatic for the patient. Further, due to the moderate temperature, which is that of hyperthermia, usually from 42° to 43° C. in the tissues to be treated, said temperature is inadequate to bring about histological modification to the BPH tissues which are not by nature malignant or cancerous. Hyperthermia has always been advocated for destroying cancerous cells which are less resistant to heat than healthy cells. However, BPH, which is the result of natural enlargement of the periurethral glands of the prostate, does not comprise cancerous cells. In this document, the transurethral probe is held in place in the urethra by the presence of a front balloon inflated in the bladder coming to be locked in the neck of the bladder.

Technomed document FR-A-2 639 238 also discloses an apparatus for the surgical treatment of prostate tissues causing destruction thereof, using an urethral probe comprising a microwave antenna, said urethral probe being provided with thermal protection means for the urethra and comprising more particularly cooling means. Thanks to this combination of an urethral probe with irradiation heating by microwaves and cooling by conduction, an effective treatment has been made possible, quite unexpectedly, in a single one-hour session, without anaesthetic, the cold having an anaesthetic effect on the nerves of the urethral wall, and without side effects such as tissue loss or retrograde ejaculation. The apparatus in accordance with said patent, marketed by Technomed under the name of Prostatron® has met with resounding commercial success, more particularly, thanks to its ability to perform necrosis of intraprostatic tissues while preserving the urethral wall intact, a result which the prior art has not been able to achieve.

The prior art is particularly suitable for the treatment of relatively large prostates for which maximum obstruction is the consequence of hypertrophy of the transition region starting in the periurethral glands and ending at a point midway between the bladder neck and the Veru montanum.

However, it happens that, in a number of cases, a non-negligible part of which is made up of prostates with a volume not exceeding 30 cm$^3$, the cause of the obstruction of the urethral canal does not lie primarily in the consequence of hypertrophy in the transition region starting in the periurethral glands, but, quite the contrary, in the hypertonicity of the muscles of the bladder neck and the intraprostatic sphincter. Likewise, in the case of prostates with a volume greater than 30 cm$^3$, examples can occur where the maximum obstacle is located at the level of the bladder neck whose hypertonicity also plays a part in obstructing the urinary tract.

SUMMARY OF THE INVENTION

The aim of the present invention is thus to solve the new technical problem consisting in providing a solution which enables the problems of prostate obstruction, preferably as a result of Benign Prostatic Hypertrophy or BPH, to be solved, at least part of which obstruction is located at the level of the bladder neck, and without having to perform resecting using a resecting device as was previously necessarily the case with conventional prostate resection, the surgeon thus removing the bladder neck with the urethral region of the prostate.

A further aim of the invention is to solve said technical problem by providing a solution which enables part of the urethral canal to be preserved at least on the lower part of the prostate below the Veru montanum, or at least to preserve the outer sphincter, i.e. the non-prostatic urethra, and the aim therein being to preserve fully or at least temporarily the intraprostatic urethra.

The present invention provides for the first time a satisfactory solution to said multiple technical problems, which is usable both industrially and medically in great safety, in a single session, without requiring the patient to be admitted to hospital, i.e. as an outpatient.

Thus, according to a first aspect, the present invention provides an urethral probe comprising a front part and a rear part, a microwave antenna linked to an external microwave generating device, wherein the microwave antenna has its primary active heating part arranged in said urethral probe to be directed at the prostate tissues situated at least at the level of the bladder neck in the working position.

According to one particularly advantageous embodiment of the invention, the urethral probe comprises in its front part an inflatable balloon, to be inflated in the bladder when the urethral probe is in position, its front part being arranged inside the bladder by being locked against the bladder neck after inflation, wherein the primary active heating part of the microwave antenna is located in the vicinity of the lower part of the balloon.

According to one particular embodiment, the primary active part of the microwave antenna is located at a distance of between 0 and 5 mm from the base of the balloon, more particularly in contact with the bladder neck, outside said balloon.

According to one particularly advantageous embodiment of the invention, the microwave antenna is a single polarity antenna, comprising a metal cable coaxial with the probe and whose external screening terminates in the vicinity of the base of the balloon for emitting microwaves primarily radially at the level of the ballon base.

According to another particular feature of the invention, the microwave antenna is designed to emit microwaves at a frequency of about 915 MHz or about 2450 MHz.

According to another particularly preferred embodiment, the bare part of the microwave antenna extends over at least part of the dimension of the front balloon intended to be locked inside the bladder at the level of the bladder neck.

According to a second independently patentable aspect, the invention provides an urethral probe means comprising a microwave antenna connected to an external microwave generating device wherein it comprises thermal protection means for the urethral canal on at least part of its length at prostate level, more particularly in the lower part of the prostate at least up to the Veru montanum, or at least across the entire dimension of the outer sphincter, in order to protect the non-prostatic urethra effectively against the heat.

The thermal protection means advantageously comprise thermal control means fed by a thermal control liquid originating in feed means external to the probe. Said thermal control means can comprise at least one inlet duct and at least one outlet duct which communicate via a joining duct.

According to one embodiment, the thermal protection means, more particularly aforesaid thermal control means, can extend over the entire length of the emitting antenna.

According to another embodiment, the urethral probe comprises aforesaid thermal protection means, more particularly aforesaid thermal protection means, at least across the dimension of the outer sphincter, said thermal protection means extending at least up to the Veru montanum, thereby effectively protecting the non-prostatic urethra against the heat.

According to another embodiment, aforesaid urethral probe comprises the first thermal protection means for the urethral canal over a distance sufficient to cover at least all the dimension of the outer sphincter, and at most up to the Veru montanum, and second thermal protection means for the urethral canal covering the entire length of the emitting antenna, so as to provide full protection of the non-prostatic urethral canal, and temporary or full thermal protection of the part of the urethral canal located above the outer sphincter, and more particularly above the Veru monatanum at least at the start of thermal treatment, according to the desired therapeutic aim.

Said first and second thermal protection means can comprise first and second thermal control means fed by a first and second thermal control liquid originating in first and second feed means external to the probe. Said first and second thermal control means can comprise at least one first and one second inlet duct and at least one first and one second outlet duct communicating by means of at least one second joining duct.

According to another particular embodiment, the thermal control means can also feed aforesaid balloon with a thermal control liquid which can be identical to that used to perform urethral thermal control, in order to avoid overheating inside the ballon, which encloses the greater part of the emitting antenna.

According to another advantageous embodiment, the urethral probe also contains means for detecting the temperature on or in the urethral probe. Preferably, said temperature detecting means comprise at least one optic fiber advantageously thermally insulated from the thermal protection means, more particularly thermal control means advantageously comprising several strands of fibers arranged so as to be longitudinally and/or axially offset in the longitudinal and/or axial direction of the probe in such a way as to detect the temperature on different longitudinal and/or axial positions of the probe.

The thermal control means are for instance comprised of thermal control ducts such as described in FIGS. 1 to 7 of the earlier document by the applicant FR-A-2 639 238 to which the expert in the field may refer.

According to a second aspect, the present invention provides an apparatus for the therapeutic treatment of tissues by thermotherapy, characterised in that it comprises an urethral probe as previously defined.

According to one particularly advantageous embodiment, the apparatus for the therapeutic treatment of tissues by thermotherapy comprises the aforesaid urethral probe comprising a microwave antenna connecting both the external device for generating microwaves and the thermal protection means for the urethral canal over at least part of its length at the level of the prostate, and more particularly in the lower part of the prostate extending at least up to the Veru montanum.

According to one particularly advantageous embodiment of the apparatus, said apparatus comprises means for adjusting the emitting power of the microwaves and for varying gradually said power from a minimum value up to a maximum value.

The apparatus preferably comprises means for regulating the temperature of said thermal control liquid at a predetermined temperature value or range of temperatures. The apparatus also preferably comprises a central control device. The central control device may, preferably, control the emitting power of the microwaves and/or the supply of thermal control liquid and temperature and/or the flow rate in at least two distinct phases, a preliminary phase during which the thermal control liquid is fed at a temperature at least temporarily lower than the body temperature of the living being to undergo the treatment optionally with at least temporarily minimum emitter power, and a final phase wherein the thermal control liquid supply is stopped and the microwave emitting power is at its maximum value compatible with the admissible maximum rectal temperature threshold.

According to one particularly advantageous embodiment, the central control device can control at least one intermediate phase during which microwave emission can advantageously be started at a minimum emitting power, the microwave emitting power is gradually increased to a maximum power value compatible with an admissible maximum rectal temperature threshold, with, optionally, simultaneously a gradual increase in the temperature of the thermal control liquid to reach gradually an urethral temperature greater than that of the body, advantageously at least 40° C.

Thus, according to a particularly advantageous embodiment, the apparatus is characterised in that it comprises in addition to rectal temperature detecting means, for instance where mounted on or in a rectal probe and transmitting the detected temperature to said central control device.

Likewise, means can be provided for controlling the position of the urethral probe which means can for instance be incorporated in a rectal probe, as described in the earlier document by the applicant FR-A-2 639 238. Said rectal probe can advantageously comprise means for detecting the temperature in the rectum so as to enable automated therapeutic treatment due to the central control device, for instance comprising a computer or microcomputer and containing at least one interface enabling the practitioner to integrate parameterisable and variable data during the treatment such as for instance the microwave emission frequency, the microwave emission power, and the temperature or range of temperatures of the thermal control liquid, the circulation rate of the thermal control liquid in the thermal control means integrated in the urethral probe, and admissible maximum temperatures in the urethra and rectum.

According to another advantageous independent embodiment, said central control device is programmed to control thermal control liquid circulation during only part of the total microwave emission time, according for instance to a first phase at a temperature lower than that of the body of a living being, more particularly a human being, at a temperature at least equal to 42° C. and even capable of reaching 45° C. and finally, according to a final phase to stop fully circulation of the thermal control liquid, the emission of microwaves continuing for a predetermined time.

According to one particular embodiment, microwaves can be emitted with a gradual increase in power from a lower level, for instance about 5 W, to an intermediate level, for instance in the order of 20 to 40 W, when the gradual increase of the thermal control liquid temperature is triggered, then lastly up to full power level, for instance in the order of 40 W to 100 W, after circulation of the thermal control liquid is stopped.

According to another advantageous independent embodiment, aforesaid central control device is programmed to control circulation of the thermal control liquid in the thermal control means over an adequate distance up to and including the full dimension of the outer sphincter, so as to thermally protect the non-prostatic urethra throughout the duration of the treatment. Advantageously, according to this embodiment, microwaves can also be emitted with a gradual increase in power from a lower level, for instance about 5 W, up to full power level which can for instance reach 100 W.

According to a further advantageous independent embodiment, said central control device is programmed to control permanently circulation of the first thermal control liquid in the first thermal control means extending over a sufficient distance up to and including the whole dimension of the outer sphincter, so as to thermally protect the non-prostatic urethra; and to control circulation of the second thermal control liquid in second circulation means extending over the whole urethra, and preferably over the entire length of the emitting antenna, said circulation of second thermal control liquid being carried out during only part of the the total microwave emission time, according for instance to a first phase at a temperature lower than that of the living being, more particularly a human being, then according to a second phase to increase gradually the temperature of the second thermal control liquid up to a temperature at least equal to that of the body of the living being, more particularly a human being, at a temperature at least equal to 42° C. and capable of reaching even 45° C. and finally, according to a final phase, to stop circulation of second thermal control liquid completely, microwave emission continuing for a predetermined time.

According to a third independently patentable aspect of the invention, said apparatus comprises means for treating by thermotherapy the tissues of the periurethral region or the bladder neck, combined with means for administering a drug with powerful pain relief effect on the heat-sensitive nerves without noticeable anaesthetic effect. Preferably, this drug has an analgaesic effect notably by acting on the central nervous system. A morphine-type drug is preferred and further said drug preferably comprises as active substance an ester or a morphine derivative, more particularly a morphine sulphate such as the drug known by the name of Moscontin®.

This drug is, for instance, administered dosed at between 10 mg and 100 mg in one dose 3 to 4 hours before thermotherapy treatment.

When performed in conjunction with a drug, the thermotherapy treatment can be performed in various ways and particularly by any device capable of applying thermotherapy and preferably thermotherapy via the urethra. Thus, in this context, it is preferable to use said urethral probe and advantageously aforesaid treatment apparatus.

According to an advantageous embodiment, provision is also made for administering an anti-inflammatory treatment to the patient after the thermotherapy treatment. The anti-inflammatory treatment preferably comprises administration of a steroid-type anti-inflammatory drug not having any anti-spasmodic effect, prescribed for instance for at least 2 weeks. Said treatment is used to limit or even prevent the consequences of oedema resulting from the thermotherapy treatment such as retention and the possibility of prostatitis which may result from an infection. Steroid-type anti-inflammatory drugs not having any anti-spasmodic effect are well known to practitioners.

According to a fourth aspect, the present invention also relates to a therapeutic process for a male living being, preferably a human being suffering from obstructed micturition troubles, and notably as a consequence of BPH, using the urethral probe or the apparatus according to the invention as provided by the description in full.

Other aims, features and advantages of the invention will be clear in the light of the following explanatory description with reference to a currently preferred embodiment of the invention given simply for illustrative purposes and which does not in any way limit the scope of the invention. In the drawings:

DETAILED DESCRIPTION OF THE PREFERRED EMBODIMENTS

Figure 1:
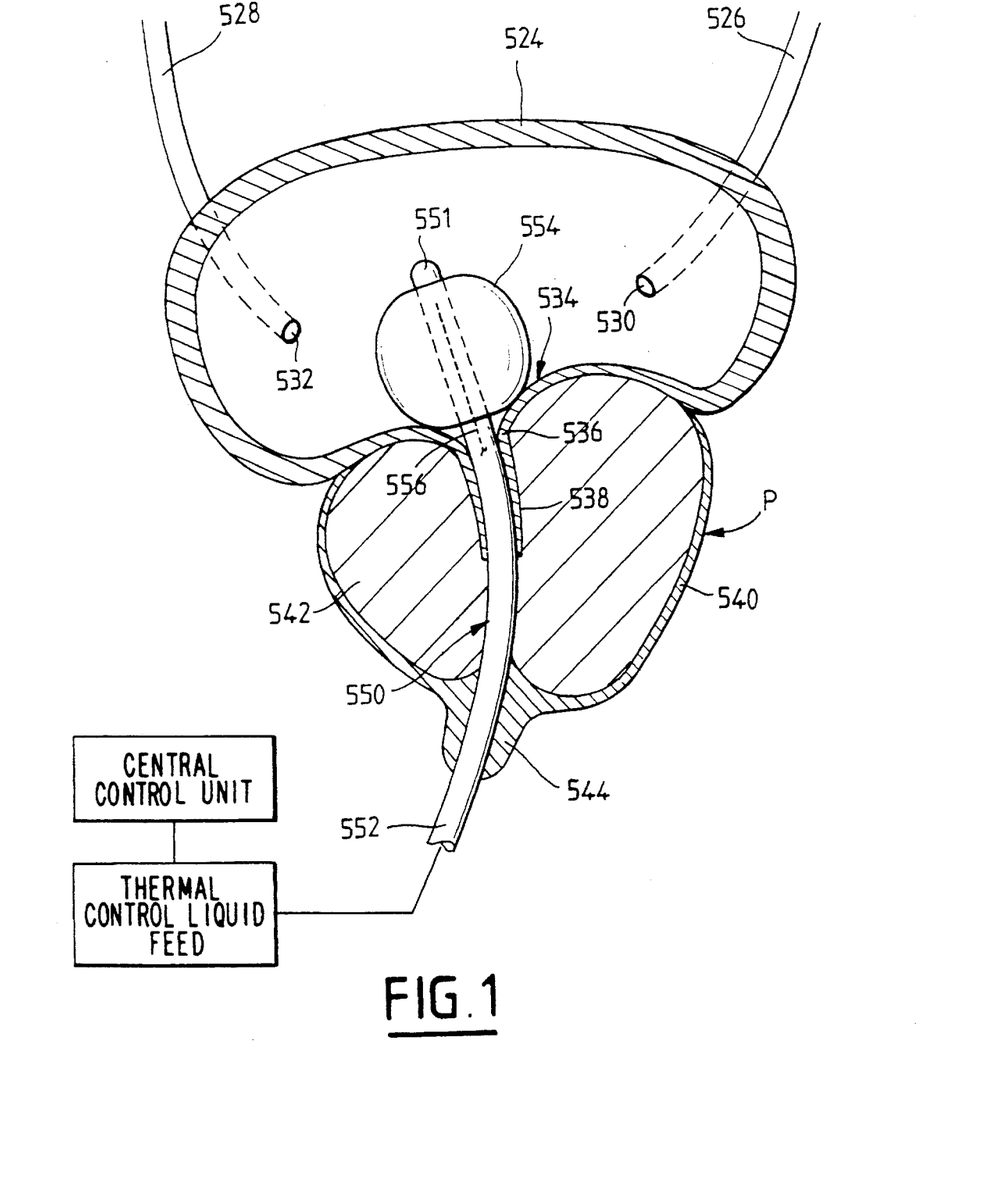
FIG. 1 is a diagrammatic view showing a longitudinal axial cross-section of the bladder and prostate with the urethral probe comprising a microwave antenna according to the present inverntion, in position in the bladder with here, according to the preferred embodiment, a front balloon in the inflated state supported on the bladder neck, said urethral probe comprising here the essential main element of an apparatus for therapeutic treatment of the prostate by thermotherapy according to the present invention.

With reference to FIG. 1, this shows diagrammatically the bladder 524 of a male human being or animal, and both ureters 526, 528 ending in the bladder via an orifice 530, 532 and connected upstream to the kidneys. The bladder neck is represented by the general reference number 534. The prostate is represented by the general reference P and comprises an outer shell 540 inside of which the prostate mass 542 is shown diagrammatically, not shown in detail here and which comprises the periurethral glands whose enlargement with aging causes Benign Prostatic Hypertrophy or BPH. The bladder neck 534 continues with the inner sphincter 536 which in turn is extended by the fibromuscular periurethral cuff 538.

The outer sphincter 544 is also located at the outlet from the prostate P.

In FIG. 1 the urethral probe is illustrated according to the present invention and has the general reference number 550. Said urethral probe 550 has a front part 551 and a rear part 552. Said urethral probe 550 is of sufficient length for its front part 551 at least to penetrate the bladder in the treatment position and its rear part 552 is connected to the general apparatus comprising all feed means and the central control device as described in detail in the earlier document FR-A-2 639 238 to which the expert may refer.

Said urethral probe 550 comprises in its front part 551 an inflatable balloon 554 shown here in the inflated state being supported on the bladder neck 534. Said urethral probe 550 also comprises a microwave antenna shown diagrammatically as a dotted line in FIG. 1 with the general reference number 556 and which will be described in greater detail with reference to FIG. 2.

According to the present invention, the microwave emitting antenna 556 is positioned in the urethral probe 550 in order to have a substantial or greater part of its primary heating power directed towards the bladder neck 534 and thus likewise the inner sphincter which is attached to the bladder neck and which to some degree is the continuation thereof.

Figures 2, 3:
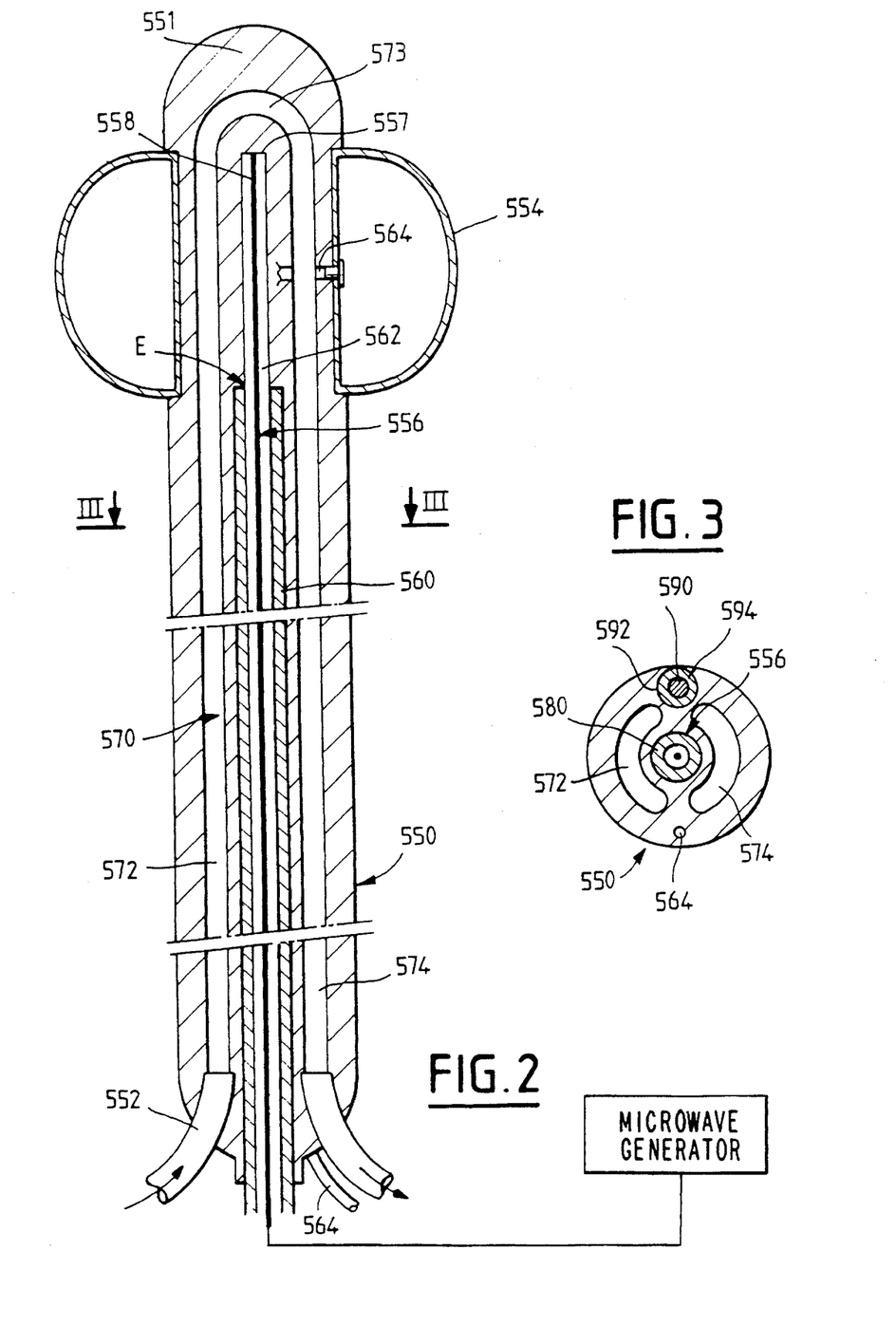
FIG. 2 is an enlarged scale longitudinal axial view in partial cross-section of the urethral probe illustrated in FIG. 1, with the balloon in the inflated state.
FIG. 3 is a cross-section view along line III—III of FIG. 2 enabling the thermal control means to be represented here as arc-shaped ducts, and the temperature detecting means and the balloon inflation conduit.

According to one advantageous embodiment, the primary active heating part E of the emitting antenna 556 is located in the vicinity of the base of the balloon 554 as is clearly shown in FIG. 2. Said primary active part E is preferably located at a distance of about 0 to 5 mm from the base of the balloon 554, more particularly when said base is in contact with the bladder neck as shown in FIG. 1.

Thus, referring to FIG. 2, this shows that the microwave antenna includes here for instance a single-pole antenna comprising a coaxial cable formed by an internal metal wire 558 and external screening 560, the internal metal wire 558 and external screening 560 being separated by an electrically insulating layer 562. It will be seen that the screening stops at a distance from the front end 557 of the antenna 556. It is known that, in a microwave antenna, the main part of the emitting power is released where the screening stops. Here screening is provided so as to stop at emission position E which is provided so as to be located at the level of the bladder neck 534 in the working position as shown in FIG. 1.

In the preferred case where the urethral probe 550 comprises at its front part 551 an inflatable ballon 554 to lock the urethral probe in position in the bladder neck, as shown in FIG. 1, provision is made, preferably and according to the structure shown, for the main emission position E, thus the position of the end of the screening 560, to be substantially located at the base of the balloon 534. Of course, certain embodiments would enable said screening stop position to be modified. However, due to the fact that the balloon 554 comes to be locked in the inflated state in the bladder neck, the position of the balloon is extremely safe and reliable. It therefore convenient and extremely safe to position the emitting part E so as to be in relation with the inflatable balloon 554.

Naturally, on account of the heating power of the microwave antenna 556, it is necessary to provide for the balloon to be made in a heat-resistant material, capable of resisting microwave antenna heating temperatures, i.e., usually in excess of 80° C.

The inflatable balloon 554 is inflated via a special inflation duct 564 which can also be seen in FIG. 3. The balloon can be inflated with air or a liquid and more particularly, if desired, by a radio-reflecting liquid such as an electrically conductive solution.

Further, the urethral probe of the invention also comprises in its mass thermal protection means 570 for protecting at least temporarily the urethra tissues in contact with the probe surface. Said thermal protection means advantageously comprise thermal control means such as at least one thermal control liquid inlet duct 572 and at least one thermal control liquid outlet duct 574, both ducts communicating in the front part of the probe via a joining duct 573. It is obvious that the thermal control liquid is fed by thermal control liquid feed means external to the probe and forming part of the general apparatus as the expert will well understand. Said external thermal control liquid supply means usually comprise heating and/or cooling means enabling the temperature of the thermal control liquid to be regulated to a value or range of predetermined temperature values. The shape of the ducts is variable as described in the earlier application by the applicant published under the number FR-A 2 639 238 to which the expert may refer. For instance, in FIG. 3, said ducts 572, 574 have the shape of an annular sector. Further, it may be advantageous for the emitter antenna 556 here forming part of a coaxial cable to be arranged in a central duct, in a removable or permanent manner.

The urethral probe can also be provided with thermal control means in the balloon 554 in such a way as to prevent overheating thereof, given that the balloon encloses the greater part of the bare emitter part 558 of the antenna 556.

The therapeutic treatment apparatus comprises externally to the probe 550 means for adjusting the emission frequency of the microwave antenna 556 and/or means for regulating microwave power. Said respective means preferably enable microwave power to be increased/decreased gradually. However, for the frequency, it is preferable that an antenna only emits at a single frequency since an antenna is built or designed in a specific way for a desired emission frequency. Nevertheless, the same antenna can be used for several frequencies if limited performance is acceptable for the frequencies for which the antenna is not specifically designed.

Provision can also be made advantageously for the urethral probe to be fitted with the temperature detecting means having the reference 590, which are clearly illustrated in FIG. 3. It is advantageous for the temperature detecting means to comprise at least one optic fiber which has the advantage of not interfering with microwave emission, which means are arranged in a special duct 592 of the urethral probe 550, and separated from the body of the probe by thermal insulation means 594 with the exception of a detecting area proper for instance so as to face the emitting antenna, in order to detect the temperature on the surface of the probe.

As described in the earlier patent by the applicant FR-A 2 639 238, means for controlling the position of the urethral probe can be provided, incorporated for instance in a rectal probe. Said means for controlling the position of the urethral probe are advantageously comprised of a rectal-type echographic probe connected to a screen echograph.

The external apparatus advantageously comprises a central control device, such as a computer or microcomputer centralising all data, and capable of automatically controlling the external device for generating microwaves in accordance with collected temperature data and data which can be programmed by the practitioner, as the expert also familiar with the commercially available Prostratron apparatus will well understand.

Due to the new urethral probe which is the subject of the present invention, the practitioner can perform therapeutic treatment on obstructive tissues, at the level of the bladder neck and/or inner sphincter and/or urethral cuff on account of the fact that the main or greater part of the primary heating power of the microwave antenna is located at the level of the bladder neck and/or inner sphincter.

Further, thanks to the central control device and the thermal control means, the practitioner can, during the first phase, circulate in the liquid thermal control or thermoregulating means a thermal control or thermoregulating liquid at a temperature at least lower than body temperature, for instance in the order of 20° C. during the preliminary phase which enables the tissues to be cooled by producing an anaesthetic effect leading to improved tolerance during heating at a later stage.

Then, in the second phase, the microwave emission is started at minimum emitting power, then the microwave emitting power is increased gradually with, optionally simultaneously, a gradual increase in the temperature of the thermal control liquid to reach gradually an urethral temperature greater than that of the body, advantageously at least 40° C., said phase being for instance called an intermediate phase.

Lastly, in the last or final phase, the command to stop the thermal control liquid supply means is given whereas the microwave emitting power is at maximum value. Said maximum power can for instance be as high as 100 W.

It is advantageous, according to the invention, for the emitting antenna 556 to be designed to emit at a frequency of 1300 MHz±50 MHz, or more preferably at a frequency of 1296 MHz.

Optionally and for special cases a frequency of 915 MHz can be used or, in other special cases, a frequency of 2450 MHz, although these frequency values are not preferred values.

Further, and due to the presence of temperature detecting means in the urethra and also advantageously in the rectum, maximum urethral and rectal temperature thresholds can be entered in the central control device comprising for instance a microcomputer or computer, which means, when said thresholds are reached, automatically command a decrease in the microwave emitting power so as not to exceed said thresholds.

It is understood that, due to the invention, natural thermal control of tissues surrounding the prostate is triggered in the preliminary phase. Said natural thermal control corresponds to an increase in blood circulation. The tissues prepare themselves to evacuate the calories provided during the final heating phase at full power.

As a result, the invention enables natural thermal protection of the tissues surrounding the prostate, particularly the rectum.

A precise example of implementing of the process according to the invention is as follows:

Firstly, the urethral probe 550 is inserted in the urethra until its front part 551 penetrates the bladder. Then, the balloon 554 is inflated via the respective duct 564 and the urethral probe 550 is withdrawn until the balloon comes to be supported on the bladder neck 534 as shown in FIG. 1.

In this position, the emitting antenna 556 has its primary active heating part facing the bladder neck and inner sphincter.

Once this is done, and after any checking by the control means such as rectal control means such as for instance a rectal echographic probe, the treatment stage proper. is proceeded with.

At the outset, the thermal control liquid is made to circulate in the thermal control means or thermoregulation means 572, 574 at a temperature lower than body temperature, i.e. a cooling temperature, for instance at 20° C. for several minutes, for instance 3 minutes.

Then, or substantially simultaneously, microwaves are emitted, for instance at a preferred frequency of 1296 MHz starting at a minumum power of 5 W which is increased gradually for instance in increments of 5 W engaged every 2 minutes until maximum power is reached, for instance 100 W.

A maximum rectal temperature threshold has for instance been set at 42.5° C. The first time said rectal temperature is reached, the gradual increase in the temperature of the cooling liquid from 20° C. to 44° C. is automatically triggered in successive increments of several degrees which can be for instance at the outset several temperature increments of 5° to 6° C., then temperature increments by half, triggered every 2 minutes.

Every time the maximum rectal temperature is reached, microwave power is decreased.

When the maximum temperature of the thermal control liquid, here for instance 44° C. and the balance of full microwave power compatible with the maximum rectal temperature threshold of 42.5° C. are reached simultaneously, according to a currently preferred embodiment, the circulation of the thermal control liquid in the thermal control means 572, 574 can be stopped and the emission of microwaves continued at the highest possible power compatible with the maximum rectal temperature threshold of 42.5° C.

By monitoring the temperature of the urethra, provision can be made for the maximum temperature threshold, for instance 75° C., to trigger an alarm.

At this stage, the therapeutic treatment for destroying irreversibly tissues of the bladder neck and/or inner sphincter is complete.

The full duration of the treatment is approximately one hour in a single session, according to a safe and reliable procedure and enable effective protection of the rectum due to triggering of the natural thermal protection of the rectum.

Finally, a cavity is obtained in the prostate next to the one which surgeons hollow out when they perform transurethral resection of BPH.

According to a second variant, it is possible to maintain circulation of the thermal control liquid throughout the treatment, in which case the urethral wall is protected and only deep tissues undergo necrosis.

According to another advantageous embodiment, provision can be made for combining this treatment with administration of drug, a drug which relieves pain due to the heat-sensitive nerves below a sensitive level for the patient.

Advantageously, a morphine-type analgaesic product will be used as a drug, preferably a morphine sulphate such as Moscontin®, in a single dose of for instance 30 mg 3 to 4 hours before starting treatment.

Thanks to the invention, it is possible to treat small prostatic volumes. It is also possible to perform full necrosis of the bladder neck in complete safety in a single session. Other advantages will be apparent to the expert.

Figures 4, 5:
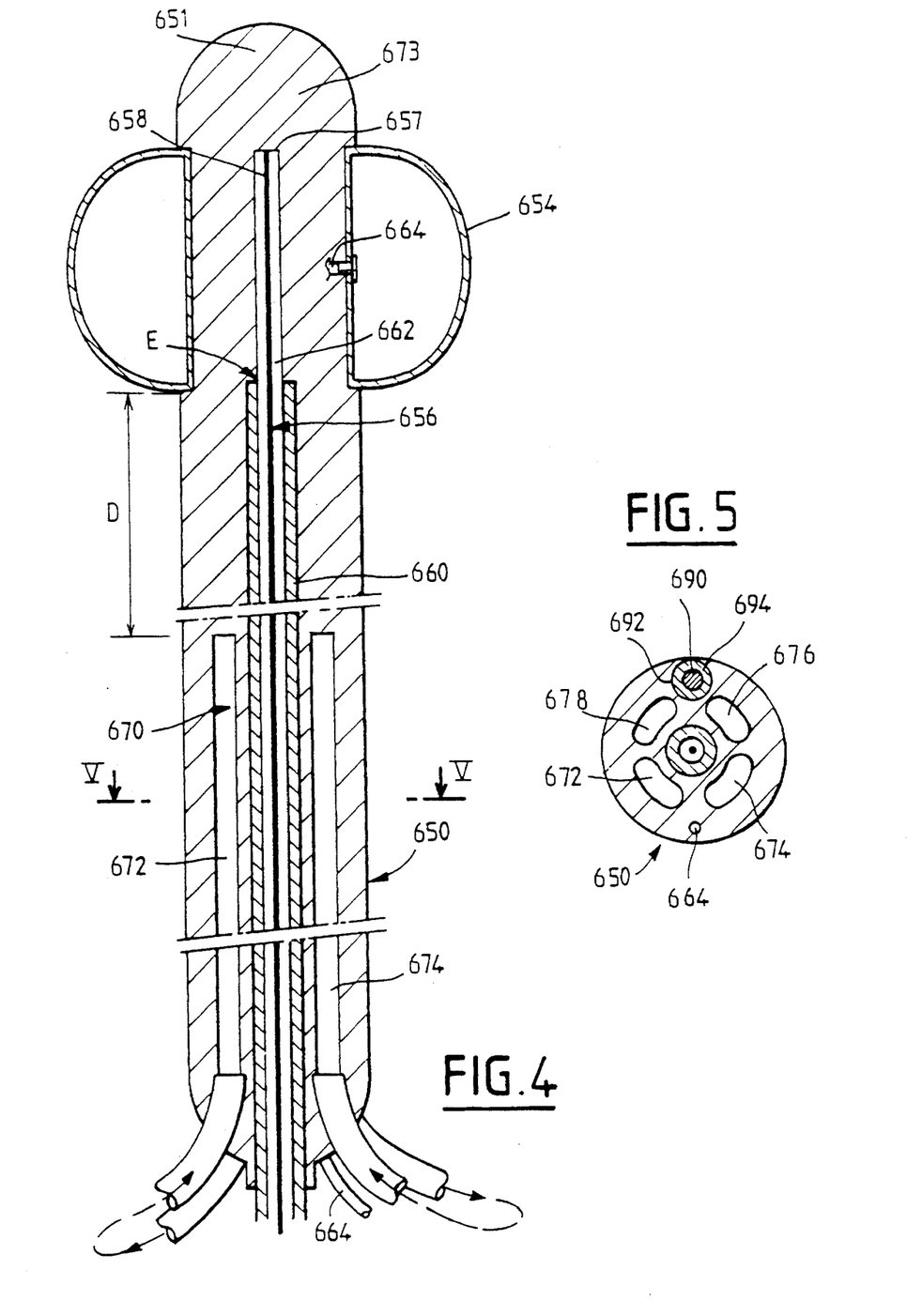
FIG. 4 is a cross-section view similar to that in FIG. 2 of a second preferred independent embodiment of the invention comprising thermal control means enabling the non-prostatic urethra to be protected.
FIG. 5 is a cross-section view along line V—V of FIG. 4.

Now it is referred to FIG. 4, which shows a second currently preferred and independently patentable embodiment of an urethral probe according to the present invention. According to said second embodiment, the same reference numbers have been used as in the embodiment in FIGS. 1 to 3 for identical parts or those fulfilling a similar function, but increased by 100. Thus, the urethral probe has the general reference number 650, the emitting antenna has the general reference number 656, and the thermal protection means the general reference number 670. Likewise, the inflatable balloon has the reference number 654 and its feed duct the reference number 664.

However, in said second embodiment, the thermal protection means 670 are shown in the form of thermal control means integrated in the probe extending over a dimension sufficient to reach and cover the full dimension of the sphincter, i.e., to thermally protect the non-prostatic urethra. Thus, said thermal protection means 670 are located at a predetermined distance D from the base of the inflatable balloon 654 to provide effective thermal protection of what is known as the prostatic urethra and more particularly the prostatic urethra situated above the Veru montanum.

Said thermal protection means 670 comprise at least one thermal control liquid inlet duct 672, 674 and at least one thermal control liquid outlet duct 676, 678 communicating respectively by means of a joining duct not shown in FIGS. 4 and 5 but which is well known to the expert and shown in FIG. 2.

According to one embodiment, as shown in FIGS. 4 and 5, in the urethral probe 650 at least two thermal control liquid inlet ducts 672, 674, and at least two outlet ducts 676, 678 are provided. For instance, the inlet duct 672 communicates with the outlet duct 676 and the inlet duct 674 with the outlet duct 678, in such a way as to provide highly efficient thermal control by means of two independent circuits in which the thermal control liquid circulates to some extent against the flow, for maximum uniformity of the thermal control temperature on the periphery of the urethral probe. The thermal control liquid can obviously come from the same liquid reserve and thus the same supply means as the expert in the field will well understand.

During therapeutic treatment, the treatment procedure, with respect to the procedure described with reference to FIGS. 1 to 3, is modified as follows:

a thermal control liquid is fed permanently through the ducts 672 to 678 comprising the thermal protection means 670, to protect effectively the non-prostatic urethra, i.e., extending at least up to the outer sphincter and optionally to the Veru montanum.

Further, microwaves can be emitted with gradual increase in power from a minimum power for instance from 5 W up to a maximum power which can, for instance, be as high as 100 W, said power then being controlled, and adjusted optionally, depending on the maximum temperature thresholds for the urethra and rectum as described for the previous embodiment in FIGS. 1 to 3.

It is understood that according to said second embodiment, the prostatic urethra is not protected from the start of the thermal treatment, and will thus be destroyed gradually.

Figures 6, 7:
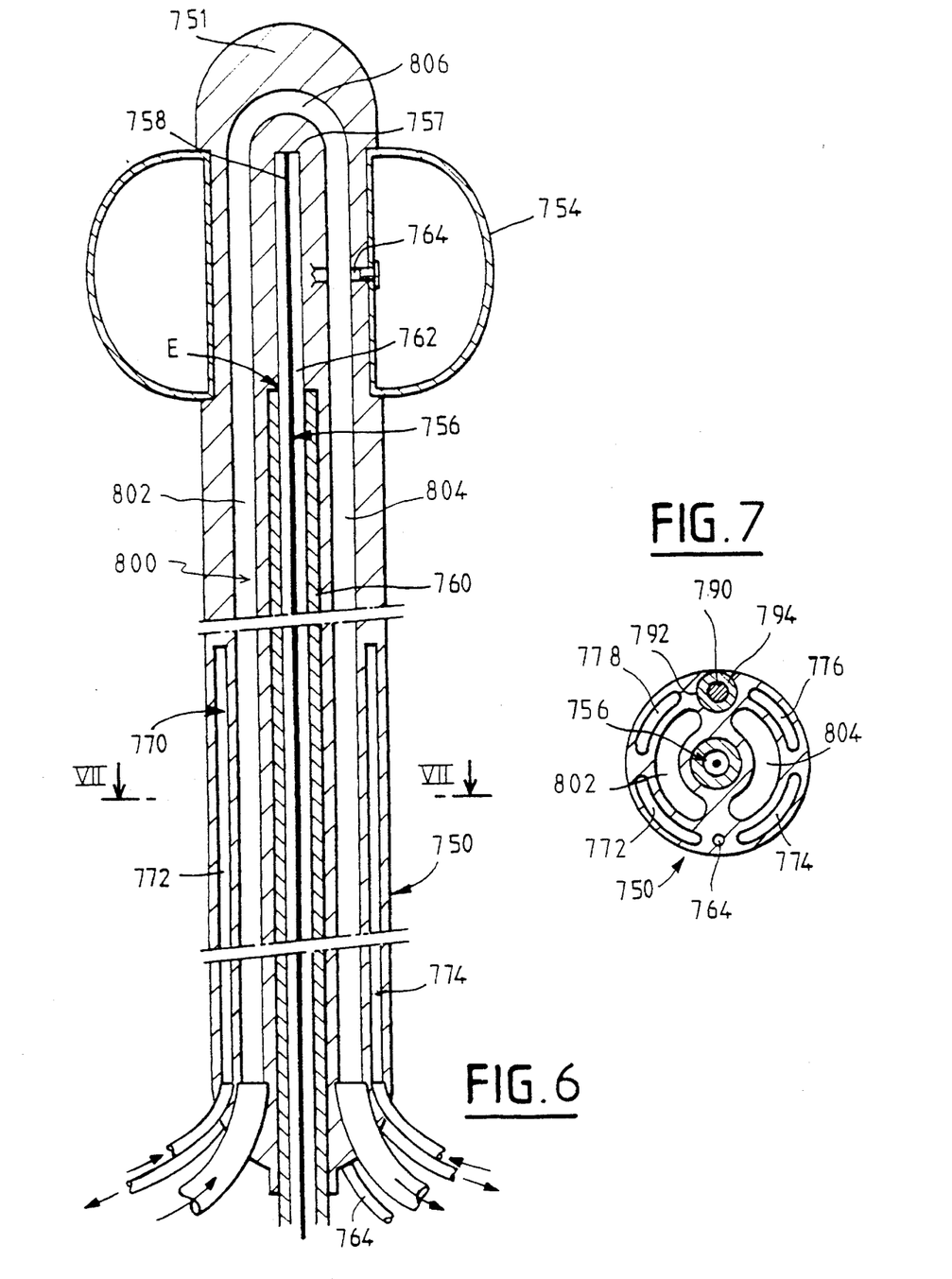
FIG. 6 is a cross-section view similiar to that in FIG. 2 of a third preferred independent embodiment of an urethral probe according to the invention, comprising first thermal protection means for protecting the non-prostatic urethra and second thermal protection means for protecting the prostatic urethra in the first stage of treatment.
FIG. 7 is a cross-section view along line VII—VII of FIG. 6.

With reference to FIGS. 6 and 7, a third independently patentable embodiment of an urethral probe is shown according to the invention for which the same reference numbers have been used for identical parts or similar functions again increased by 100.

It will be seen that the said third embodiment is based on a combination of the first embodiment in FIGS. 1 to 3 and the second embodiment in FIGS. 4 and 5.

Thus, in the urethral probe 750, first thermal protection means 770 and second thermal protection means 800 are provided.

The first thermal protection means 770 are, for instance, similar to those described with reference to FIGS. 4 and 5 and comprise at least one inlet duct 772, 774 and at least one outlet duct 776, 778 for the thermal control liquid, extending across a dimension sufficent to protect the non-prostatic urethra, i.e., at least up to the full dimension of the outer sphincter and capable optionally of reaching the Veru montanum.

In said third embodiment, the second thermal protection means 800 comprise at least one inlet duct 802 for a second thermal control liquid and communicating with at least one outlet duct 804 via a joining duct 806, ducts 802 and 804 extending over the whole length of the emitting antenna 756 as is clearly shown in FIG. 6, so as to enable temporary thermal protection of the prostatic urethra extending up to the bladder.

The therapeutic treatment procedure within the scope of the third embodiment is clearly apparent to the expert and is essentially as follows:

the first thermal control liquid with a predetermined temperature or range of temperatures is fed permanently in the first thermal control means 770 to protect the non-prostatic urethra from damage by heat throughout the thermal treatment.

a second thermal control liquid is supplied in the second thermal protection means 802 in the manner described as part of the first embodiment of FIGS. 1 to 3.

Thus, in the first phase, the practitioner makes circulate in the second thermal protection means 802 a second thermal control liquid at a temperature at least lower than the body temperature, for instance in the order of 20° C. to cool the tissues by producing an anaesthetic effect to improve tolerance during heating at a later stage.

Then, in the second phase, the command is given to stop the means for feeding the second liquid in the thermal protection means 802, while the microwave emitting power is at its maximum power which can reach 100 W.

The emission of microwaves is continued whilst ensuring that the maximum temperature thresholds for the urethra and rectum are not exceeded and via automatic command by the aforesaid central control device to decrease microwave emitting power so as to remain below said thresholds.

Within this framework, it is possible in all circumstances to ensure preservation of the non-prostatic urethra whilst enabling the practitioner to destroy the prostatic urethra at the desired moment, notably at the end of treatment, thereby enabling destruction firstly of the furthest intraprostatic tissues on account of urethral cooling performed initially in the prostate, then ending with the destruction of the tissues closest to the urethra, and including the prostatic urethra, at the end of treatment.

This procedure is particularly effective in the treatment of obstructive problems of the prostate linked to BPH.

It should be noted that the embodiments as shown in the drawings are an integral part of the present invention and are therefore an integral part of the present description. The invention also comprises all the technical means comprising technical equivalents of the described means and their various combinations.

The invention covers any feature whatsoever that appears to be new with respect to the state of the art whatsoever from the above description in its in entirety, exemplified by the drawings which form an integral part thereof.

We claim:

1. A urethral probe, comprising: an elongated tubular body having a front part, a middle part and a rear part; microwave antenna means connectable to an external microwave generating device for emitting microwaves, the probe being insertable into a prostate and bladder; and means for positioning the probe into a working position in which the middle part is in the prostate and the front part projects from the middle part into the bladder, the microwave antenna means having a primary active heating part arranged in the probe at a predetermined distance from a distal end of the front part so that in the working position microwave radiation is directed onto prostatic tissues situated mainly at a level of the bladder neck.

2. The urethral probe of claim 1, and further comprising an inflatable balloon arranged at the front part, the inflatable balloon being arrangable in the bladder in an inflated state so as to be locked against the bladder neck, the primary active heating part of the microwave antenna means being located near a lower part of the balloon.

3. The urethral probe of claim 2, wherein the primary active heating part of the microwave antenna means is arranged externally of the balloon at a distance of about 0–5 mm from a base of the balloon.

4. The urethral probe of claim 2, wherein the microwave antenna means is a single polarity antenna.

5. The urethral probe of claim 4, wherein the microwave antenna means is a coaxial cable having an internal metal wire and an external screening which ends near the lower part of the balloon.

6. The urethral probe of claim 2, and further comprising thermal protection means provided on the probe body for protecting urethral tissue from thermal damage, the thermal protection means including ducts arranged in the probe body to permit fluid flow therein, a thermal control liquid and feed means external to the probe body for circulating the thermal control liquid through the ducts, the thermal protection means further including thermal control means provided in the balloon to prevent overheating of the balloon.

7. The urethral probe of claim 1, and further comprising thermal protection means provided on the probe body for protecting urethral tissue from thermal damage.

8. The urethral probe of claim 7, wherein the thermal protection means is arranged on the probe body so as to be in a lower part of the prostate and extend at least up to the Veru montanum when in the working position.

9. The urethral probe of claim 7, wherein the thermal protection means includes ducts arranged in the probe body to permit fluid flow therein, a thermal control liquid and feed means external to the probe body for circulating the thermal control liquid through the ducts.

10. The urethral probe of claim 9, wherein the ducts include at least one inlet duct and at least one outlet duct communicating via a joining duct.

11. The urethral probe of claim 1, wherein the microwave antenna means is operative to emit microwaves at a frequency of about 1,300 MHz±50 MHz.

12. The urethral probe of claim 11, wherein, the microwave antenna means is operative to emit microwaves at a frequency of about 1,296 MHz.

13. The urethral probe of claim 1, and further comprising temperature detection means for detecting probe temperature.

14. An apparatus for therapeutic treatment of tissues by thermotherapy, comprising: a urethral probe having an elongated tubular body with a front part, a middle part and a rear part, the probe being insertable into a prostate and bladder; means for positioning the probe into a working position in which the middle part is in the prostate and the front part projects from the middle part into the bladder; and a microwave antenna connectable to an external microwave generating device and mounted within said probe body, the microwave antenna having a primary active heating part arranged in said urethral probe at a predetermined distance from a distal end of the front part so as to direct microwave radiation onto prostatic tissues situated mainly at a level of the bladder neck when the probe is in the working position.

15. The apparatus of claim 14, and further comprising temperature control means for controlling probe temperature, said temperature control means including passages within the probe body, a thermal control liquid, and feed means external to the probe body for circulating the thermal control liquid through the passages and still further comprising central control means for controlling the temperature control means so that the liquid is maintained to one of a predetermined temperature value and a range of temperature values.

16. The apparatus of claim 15, wherein the central control means is operative to control at least one of microwave emitting power and thermal control liquid feed at at least one of a temperature and a flow rate in at least two distinct phases, said distinct phases including a preliminary phase during which the thermal control liquid is fed at a temperature at least temporarily lower than body temperature of a living being undergoing treatment, and a final phase wherein the thermal control liquid feed is stopped and the microwave emitting power is at a maximum value compatible with an admissible maximum rectal temperature threshold.

17. The apparatus of claim 16, wherein the central control means is operative to control the microwave emitting power to a minimum value at least temporarily during the preliminary phase.

18. The apparatus of claim 15, wherein the central control means is operative to control at least one intermediate phase during which microwave emission is started at a minimum emitting power, and gradually increase microwave emission power to a maximum power value compatible with an admissible maximum rectal temperature threshold.

19. The apparatus of claim 18, wherein the central control means is operative to simultaneously gradually increase the temperature of the thermal control liquid until a urethral temperature greater than the body temperature is reached, and gradually increase the microwave emission power.

20. The apparatus of claim 19, wherein the central control means is operative to gradually control the temperature of the thermal control liquid until the urethral temperature is gradually increased to at least 40° C.

21. The apparatus of claim 15, and further comprising a rectal probe and rectal temperature detection means arranged at the rectal probe, for transmitting a detected rectal temperature to the central control means, the rectal temperature detection means being in operative communication with the central control means.

22. The apparatus of claim 15, and further comprising means for controlling the correct position of the urethral probe relative to the bladder neck.

23. The apparatus of claim 14, and further comprising power adjusting means for gradually adjusting microwave emitting power between a minimum power value and a maximum power value, and still further comprising a central control unit operatively connected to said power adjusting means to control said power adjusting means.

24. A method for therapeutical treatment of a living being, including a human, suffering from an obstructed micturition problem, comprising the steps of: providing a urethral probe including a front part, a rear part, and a microwave antenna connected to an external microwave generating device, wherein the microwave antenna has a primary active heating part (E) arranged in the urethral probe; positioning the probe into a working position in a urethral canal so that the primary active heating part of the antenna is directed onto prostatic tissues situated at a level of a bladder neck; and, activating said microwave generating device to generate microwaves through said microwave antenna at a microwave emitting power and during a period of time sufficient to reach necrosis of the prostatic tissue situated mainly at the level of the bladder neck in the probe working position.

25. The method of claim 24, and further comprising providing said urethral probe with means for thermally protecting at least a partial length of the urethral canal up to the level of the prostate; and activating said thermal protection means of the urethral canal during a period of time where thermal protection of the urethral canal is desired.

26. The method of claim 25, including thermally protecting the urethral canal up to the lower part of the prostate extending at least up to the Veru montanum.

27. The method of claim 25, wherein the step of providing means for thermally protecting the urethral canal includes providing thermal protection means comprising thermal control means supplied with a thermal control liquid originating in feed means external to the probe, and a central control device acting on said thermal control means during at least a part of said treatment for maintaining the temperature of said thermal control liquid at one of a predetermined value and a range of temperature values.

28. The method of claim 27, and further comprising the steps of: providing means for adjusting the microwave emitting power, controlling thermal control liquid feed at at least one of a temperature and a flow rate in a preliminary phase during which the thermal control liquid is fed at a temperature at least temporarily lower than the body temperature of the living being undergoing treatment, and in a final phase in which the thermal control liquid feed is stopped and the microwave emitting power is at its maximum value compatible with an admissible maximum rectal temperature threshold.

29. The method of claim 28, including adjusting the microwave emitting power to a minimum value at least temporarily during the preliminary phase.

30. The method of claim 27, including controlling at least one intermediate phase with the central control device during which microwave emission is started at a minimum emitting power, so that the microwave emission gradually increases up to a maximum power value compatible with an admissible maximum rectal temperature threshold.

31. The method of claim 30, including simultaneously gradually increasing the temperature of the thermal control liquid until a urethral temperature greater than that of the body is reached.

32. The method of claim 31, including increasing the urethral temperature to at least 40° C.

33. The method of claim 24, and further comprising controlling the correct position of the urethral probe related to the bladder neck.

34. The method of claim 24, comprising increasing the tissues of the bladder neck of the bladder of human beings.

35. An apparatus for therapeutic treatment of tissues of a bladder neck of a bladder of a human being by thermotherapy, comprising: a urethral probe having an elongated tubular body with a front part, a middle part and a rear part, the probe being insertable into a prostate and the bladder; means for positioning the probe into a working position in which the middle part is in the prostate and the front part projects from the middle part into the bladder; and a microwave antenna connectable to an external microwave generating device and mounted within said probe body, the microwave antenna having a primary active heating part arranged in said urethral probe at a predetermined distance from a distal end of the front part so as to direct microwave radiation onto prostatic tissues situated mainly at a level of the bladder neck when the probe is in the working position.

* * * * *